(12) United States Patent
Garcia

(10) Patent No.: US 9,756,826 B2
(45) Date of Patent: Sep. 12, 2017

(54) LETTUCE VARIETY 45-90 RZ

(71) Applicant: RIJK ZWAAN ZAADTEELT EN ZAADHANDEL B.V., De Lier (NL)

(72) Inventor: Maria Tomas Garcia, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 14/840,722

(22) Filed: Aug. 31, 2015

(65) Prior Publication Data

US 2016/0060649 A1     Mar. 3, 2016

Related U.S. Application Data

(60) Provisional application No. 62/044,636, filed on Sep. 2, 2014.

(51) Int. Cl.
*A01H 5/12* (2006.01)
*C12Q 1/68* (2006.01)

(52) U.S. Cl.
CPC ............ *A01H 5/12* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 7,427,699 B1 *   9/2008   Skrsyniarz ............... A01H 5/12
                                                              435/410
9,125,375 B2 *   9/2015   Garcia .................... A01H 5/12

OTHER PUBLICATIONS

IBEB press release New race of Bremia lactucae 81:27 identified and nominated, May 2010; Plantum NL, Postbus 462, 2800 Al Gouda.
Michelmore R. & Ochoa. O. Breeding Crisphead Lettuce. In: California Lettuce Research Board, Annual Report 2005-2006, 2006, Salinas, California, pp. 55-68.
Schettini, T.M., Legg, E.J., Michelmore, R.W., 1991. Insensitivity to metalaxyl in California populations of Bremia lactucae and resistance of California lettuce cultivars to Downy Mildew, Disease Control and Pest Management, pp. 64-70.
van Ettekoven, K. et al., Identification and denomination of 'new' races of Bremia lactucae, In: Lebeda, A. and Kristkova, E (eds.), Eucarpia Leafy Vegetables, 1999.
van der Arend et al. Identification and denomination of "new" races of Bremia lactucae in Europe by IBEB until 2002. In: Van Hintum, Th et al. (eds.), Eucarpia Leafy Vegetables.

* cited by examiner

*Primary Examiner* — Eileen O Hara
(74) *Attorney, Agent, or Firm* — Vedder Price P.C.; Thomas J. Kowalski; Deborah L. Lu

(57) ABSTRACT

The present invention relates to a *Lactuca sativa* seed designated 45-90 RZ, which may exhibit a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves. The present invention also relates to a *Lactuca sativa* plant produced by growing the 45-90 RZ seed. The invention further relates to methods for producing the lettuce cultivar, represented by lettuce variety 45-90 RZ.

35 Claims, 2 Drawing Sheets
(2 of 2 Drawing Sheet(s) Filed in Color)

LETTUCE VARIETY 45-90 RZ

RELATED APPLICATIONS AND INCORPORATION BY REFERENCE

This application claims benefit of and priority to U.S. provisional patent application Ser. No. 62/044,636, filed Sep. 2, 2014.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new lettuce (*Lactuca sativa*) variety which may exhibit a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

BACKGROUND OF THE INVENTION

All cultivated forms of lettuce belong to the highly polymorphic species, *Lactuca sativa*, which is grown for its edible head and leaves. As a crop, lettuces are grown commercially wherever environmental conditions permit the production of an economically viable yield.

*Lactuca sativa* is in the Cichoreae tribe of the Asteraceae (Compositae) family. Lettuce is related to chicory, sunflower, aster, scorzonera, dandelion, artichoke and chrysanthemum. Sativa is one of about 300 species in the genus *Lactuca*.

Lettuce cultivars are susceptible to a number of pests and diseases such as downy mildew (*Bremia lactucae*). Every year this disease leads to millions of dollars of lost lettuce crop throughout the world. Downy mildew (*Bremia lactucae*) is highly destructive on lettuce grown at relatively low temperature and high humidity. Downy mildew is caused by a fungus, *Bremia lactucae*, which can be one of the following strains: NL1, NL2, NL4, NL5, NL6, NL7, NL10, NL12, NL13, NL14, NL15, NL16, Bl:17, Bl:18, Bl:20, Bl:21, Bl:22, Bl:23, Bl:24, Bl:25, Bl:26, Bl:27, Bl:28, Bl:29, Bl:30, Bl:31 (Van Ettekoven, K. et al., "Identification and denomination of 'new' races of *Bremia lactucae*," In: Lebeda, A. and Kristkova, E (eds.), Eucarpia Leafy Vegetables, 1999, Palacky University, Olomouc, Czech Republic, pp. 171-175; Van der Arend et al. "Identification and denomination of "new" races of *Bremia lactucae* in Europe by IBEB until 2002." In: Van Hintum, Th et al. (eds.), Eucarpia Leafy Vegetables Conference 2003, Centre for Genetic Resources, Wageningen, The Netherlands, p. 151; Plantum NL (Dutch association for breeding, tissue culture, production and trade of seeds and young plants), Van der Arend et al. "Identification and denomination of "new" races of *Bremia lactucae* in Europe by IBEB until 2002." In: Van Hintum, Th et al. (eds.), Eucarpia Leafy Vegetables Conference 2003, Centre for Genetic Resources, Wageningen, The Netherlands, p. 151; Plantum NL (Dutch association for breeding, tissue culture, production and trade of seeds and young plants); IBEB press release " New race of *Bremia lactucae* Bl:27 identified and nominated", May 2010; Plantum NL (Dutch association for breeding, tissue culture, production and trade of seeds and young plants), "New race of *Bremia lactucae* Bl:28 identified and nominated", March 2011; Plantum NL (Dutch association for breeding, tissue culture, production and trade of seeds and young plants), IBEB press release, "New races of *Bremia lactucae*, Bl:29, Bl:30 and Bl:31 identified and nominated", August 2013), Ca-I, Ca-IIA, Ca-IIB, Ca-III, Ca-IV (Schettini, T. M., Legg, E. J., Michelmore, R. W., 1991. Insensitivity to metalaxyl in California populations of *Bremia lactucae* and resistance of California lettuce cultivars to downy mildew. Phytopathology 81(1). p. 64-70), and Ca-V, Ca-VI, Ca-VII, Ca-VIII (Michelmore R. & Ochoa. O. "Breeding Crisphead Lettuce."In: California Lettuce Research Board, Annual Report 2005-2006, 2006, Salinas, Calif., pp. 55-68).

Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the fungus progresses to this degree, the head cannot be harvested. Less severe damage requires the removal of more leaves than usual, especially when the lettuce reaches its final destination.

Yield is an important factor for a profitable production of iceberg lettuce. Yield is based on the number of harvested heads per acre and their head weight. Especially when iceberg lettuce is used for processing and sold as a pre-cut, pre-washed product, higher yields are the driving factor to reduce raw product cost. High head weights can only be reached when the heads are large sized with sufficient volume. Smaller-sized, very dense heads are more prone to tipburn problems. A large head size also provides sufficient space inside the head for further growing. Especially when the supply of lettuce is high due to favorable weather conditions, large-headed lettuce varieties provide more flexibility to delay the moment of harvest.

Citation or identification of any document in this application is not an admission that such document is available as prior art to the present invention.

SUMMARY OF THE INVENTION

There exists a need, therefore, for a lettuce variety which exhibits a combination of traits resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

The present invention addresses this need by providing a new type of lettuce (*Lactuca sativa*) variety, designated 45-90 RZ. Lettuce cultivar 45-90 RZ exhibits a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

The present invention provides seeds of lettuce cultivar 45-90 RZ, which have been deposited with the National Collections of Industrial, Marine and Food Bacteria (NCIMB) in Bucksburn, Aberdeen AB21 9YA, Scotland, UK and have been assigned NCIMB Accession No. 42275.

In one embodiment, the invention provides a lettuce plant designated 45-90 RZ, representative seed of which have been deposited under NCIMB Accession No. 42275, wherein said lettuce plant may comprise a combination of traits resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

In one embodiment, the invention provides a lettuce plant designated 45-90 RZ which may exhibit a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, a very large head size, very large plant diameter, and large sized leaves, as well as resistance against and root aphids (*Pemphigus bursarius*), representative seed of which have been deposited under NCIMB Accession No. 42275.

In one embodiment, the invention provides a lettuce plant designated 45-90 RZ which may exhibit a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, and strong blistering, representative seed of which have been deposited under NCIMB Accession No. 42275.

In one embodiment, the invention provides a lettuce plant designated 45-90 RZ which may exhibit a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, and strong blistering, as well as resistance against and root aphids (*Pemphigus bursarius*), representative seed of which have been deposited under NCIMB Accession No. 42275.

In one embodiment, the invention provides a lettuce plant designated 45-90 RZ, representative seed of which have been deposited under NCIMB Accession No. 42275.

In an embodiment of the present invention, there also is provided parts of a lettuce plant of the invention, which may include parts of a lettuce plant exhibiting a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, or parts of a lettuce plant having any of the aforementioned resistance(s) and a combination of traits including one or more morphological or physiological characteristics tabulated herein, including parts of lettuce variety 45-90 RZ, wherein the plant parts are involved in sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts may come from include those wherein representative seed of which has been deposited under NCIMB Accession No. 42275 or lettuce variety or cultivar designated 45-90 RZ, as well as seed from such a plant, plant parts of such a plant (such as those mentioned herein) and plants from such seed and/or progeny of such a plant, advantageously progeny exhibiting such combination of such traits, each of which, is within the scope of the invention; and such combination of traits.

In another embodiment there is a plant grown from seeds, representative seed of which having been deposited under NCIMB Accession No. 42275.

In a further embodiment there is a plant regenerated from the above-described plant parts or regenerated from the above-described tissue culture. Advantageously such a plant may have morphological and/or physiological characteristics of lettuce variety 45-90 RZ and/or of a plant grown from seed, representative seed of which having been deposited under NCIMB Accession No. 42275—including without limitation such plants having all of the morphological and physiological characteristics of lettuce variety 45-90 RZ and/or of plant grown from seed, representative seed of which having been deposited under NCIMB Accession No. 42275. Advantageously, such a plant demonstrates the traits of resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

Accordingly, in still a further embodiment, there is provided a lettuce plant having all of the morphological and physiological characteristics of lettuce variety 45-90 RZ, representative seed of which having been deposited under NCIMB Accession No. 42275. Such a plant may be grown from the seeds, regenerated from the above-described plant parts, or regenerated from the above-described tissue culture. A lettuce plant having any of the aforementioned resistance(s), and one or more morphological or physiological characteristics recited or tabulated herein, and a lettuce plant advantageously having all of the aforementioned resistances and the characteristics recited and tabulated herein, are preferred. Parts of such plants—such as those plant parts above-mentioned—are encompassed by the invention.

In one embodiment, there is provided a method for producing a progeny of lettuce cultivar 45-90 RZ which may comprise crossing a plant designated 45-90 RZ with itself or with another lettuce plant, harvesting the resultant seed, and growing said seed.

In a further embodiment there is provided a progeny plant produced by sexual or vegetative reproduction, grown from seeds, regenerated from the above-described plant parts, or regenerated from the above-described tissue culture of the lettuce cultivar or a progeny plant thereof, representative seed of which having been deposited under NCIMB Accession No. 42275. The progeny may have any of the aforementioned resistance(s), and one or more morphological or physiological characteristics recited or tabulated herein, and a progeny plant advantageously having all of the aforementioned resistances and the characteristics recited and tabulated herein, are preferred. Advantageously, the progeny demonstrate the traits of resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

Progeny of the lettuce variety 45-90 RZ may be modified in one or more other characteristics, in which the modification is a result of, for example and without limitation, mutagenesis or transformation with a transgene.

In still another embodiment, the present invention provides progeny of lettuce cultivar 45-90 RZ produced by sexual or vegetative reproduction, grown from seeds, regenerated from the above-described plant parts, or regenerated from the above-described tissue culture of the lettuce cultivar or a progeny plant thereof, in which the regenerated plant shows a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

In still a further embodiment, the invention provides a method of producing a hybrid lettuce seed which may comprise crossing a first parent lettuce plant with a second parent lettuce plant and harvesting the resultant hybrid lettuce seed, in which the first parent lettuce plant or the second parent lettuce plant may be a lettuce plant of the invention, e.g. a lettuce plant having a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves and one or more morphological or physiological characteristics tabulated herein, including a lettuce plant of lettuce cultivar 45-90 RZ, representative seed of which having been deposited under 42275.

In another embodiment, the invention provides producing a lettuce plant having a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves which may comprise: crossing a mother lettuce plant with a father lettuce plant to produce a hybrid seed; growing said hybrid seed to produce a hybrid plant; selfing said hybrid plant to produce F2 progeny seed; growing said F2 progeny seed to produce F2-plants; selecting said F2-plants for exhibiting a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

Advantageously the selfing and selection may be repeated; for example at least once, or at least twice, thrice, four times, five times, six times or more, to produce F3 or F4 or F5 or F6 or subsequent progeny, especially as progeny from F2 may exhibit the aforementioned combination of traits, and may be desirable.

In still a further embodiment, the invention provides a method of producing a lettuce cultivar containing a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

The invention even further relates to a method of producing lettuce which may comprise: (a) cultivating to the vegetative plant stage a plant of lettuce variety 45-90 RZ, representative seed of which having been deposited under NCIMB Accession No. 42275, and (b) harvesting lettuce leaves or heads from the plant. The invention further comprehends packaging and/or processing the lettuce plants, heads or leaves.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

The Deposit with NCIMB Ltd, Ferguson Building, Craibstone Estate, Bucksburn, Aberdeen AB21 9YA, UK, on Aug. 22, 2014, under deposit accession number 42275 was made pursuant to the terms of the Budapest Treaty. Upon issuance of a patent, all restrictions upon the deposit will be removed, and the deposit is intended to meet the requirements of 37 CFR §1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application filed contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings, in which.

DETAILED DESCRIPTION OF THE INVENTION

Figure 1:
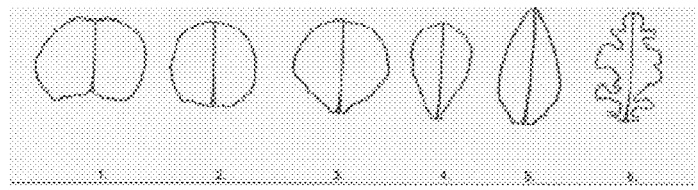
FIG. 1 is an illustration of six different shapes of the fourth leaf from a 20-day old seedling grown under optimal conditions.
Figure 2:
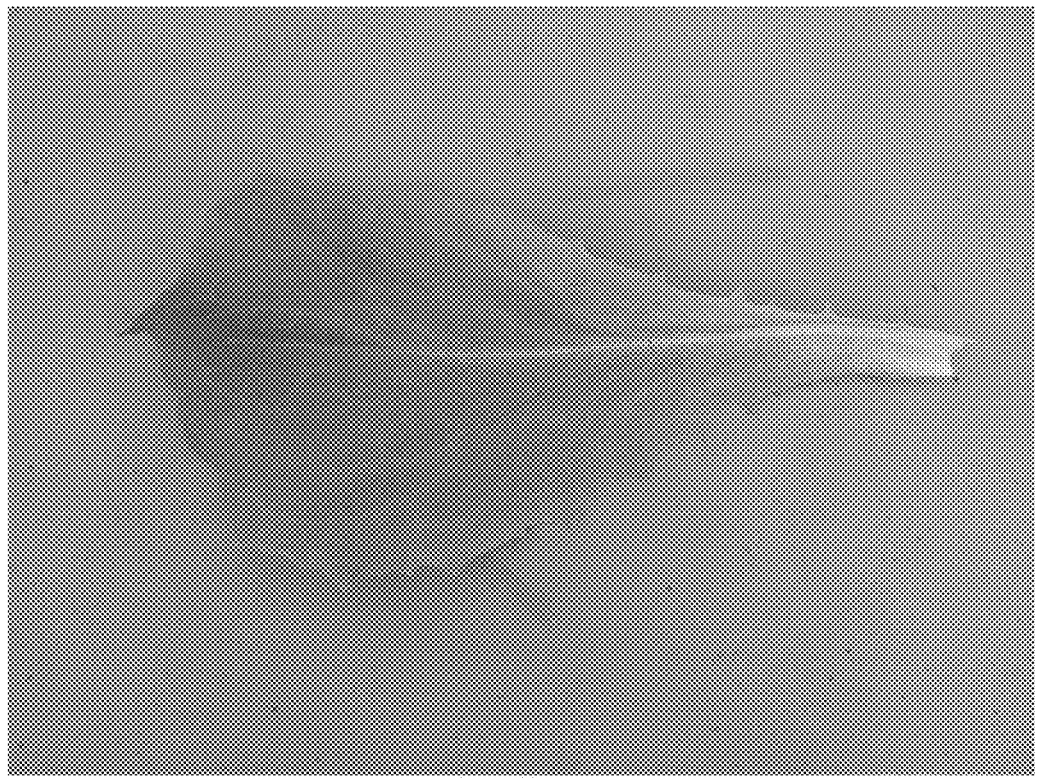
FIG. 2 is a picture of the shape of the fourth leaf of 45-90 RZ.
Figure 3:
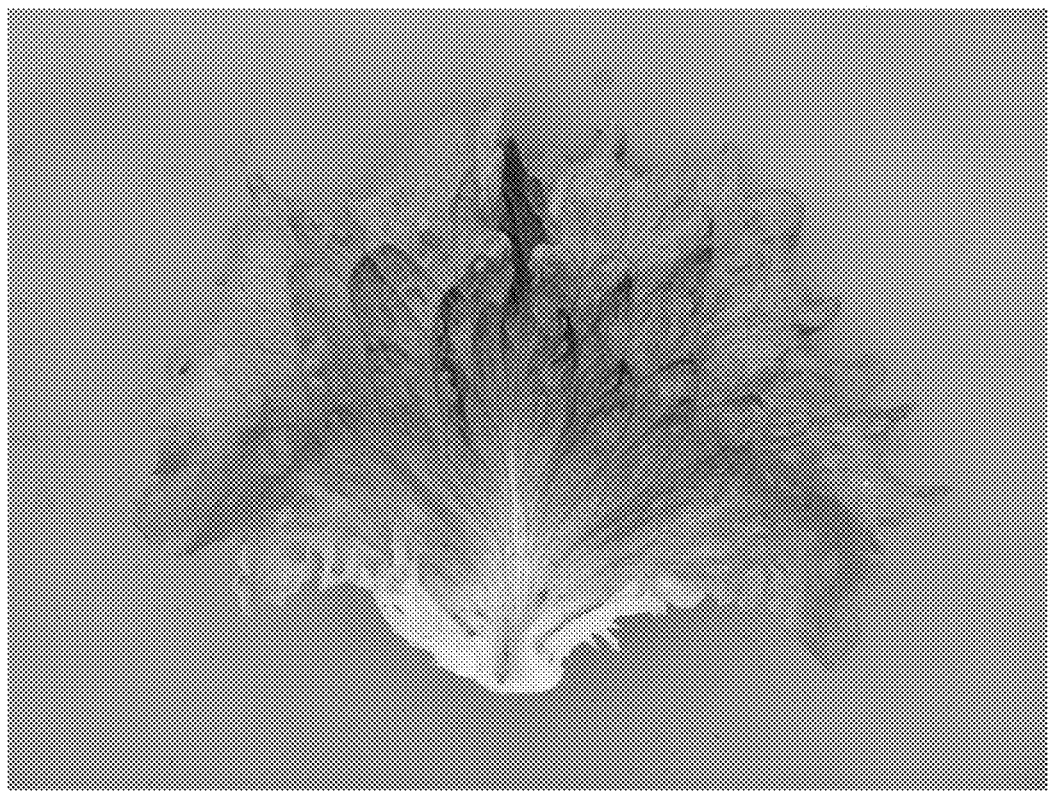
FIG. 3 is a picture of the shape of a mature leaf of 45-90 RZ.

The invention provides methods and compositions relating to plants, seeds and derivatives of a new lettuce variety herein referred to as lettuce variety 45-90 RZ. Lettuce variety 45-90 RZ is a uniform and stable line, distinct from other such lines.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

When pedigree selection is applied, in general selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype may be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

A detailed description of the development of lettuce variety 45-90 RZ is described in Table 1. Seedlot 13R.993829, was deposited with the NCIMB under deposit number 42275.

TABLE 1

| Year | Description | Location |
| --- | --- | --- |
| 0 | Final F1-cross plants 07M.81096 × 07M.81144 under glasshouse conditions | Murcia, Spain |
| 1 | F1 plant grown for F2 seed production under glasshouse conditions | Murcia, Spain |
| 2 | F2 plant 09M.84720 selected in open field followed by F3 seed 09M.612300 | Murcia, Spain |
| 3 | F3 plant 10M.81366 selected in open field, followed by F4 seed 10M.618901 | Murcia, Spain |
| 4 | F4 plant 11M.80602 selected in open field, followed by F5 seed 11M.625894 | Murcia, Spain |
| 5 | F5 plant 12M.82874 selected in open field, followed by F6 seed 12M.631213 | Murcia, Spain |
| 6 | F6 line 13R.993829 established uniform, multiplied in glasshouse, in: seed lot 13R.3829 | Hoek van Holland, The Netherlands |

In one embodiment, a plant of the invention may have all the morphological and physiological characteristics of lettuce variety 45-90 RZ. These characteristics of a lettuce plant of the invention, e.g. variety 45-90 RZ, are summarized in Tables 2 and 3.

Next to the morphological and physiological characteristics mentioned in Tables 2 and 3, a plant of the invention may also exhibit resistance to downy mildew (*Bremia lactucae* Regel.).

As used herein resistance against *Bremia lactucae* is defined as the ability of a plant to resist infection by each of the various strains Bl:1-Bl:26, Bl:28, Bl:31, Ca-I to Ca-VIII of *Bremia lactucae* Regel. in all stages between the seedling stage and the harvestable plant stage. Bl:1-Bl:26, Bl:28, Bl:31 means strains NL1, NL2, NL4, NL5, NL6, NL7, NL10, NL12, NL13, NL14, NL15, NL16, Bl:17, Bl:18, Bl:20, Bl:21, Bl:22, Bl:23, Bl:24, Bl:25, Bl:26, Bl:28, Bl:31 (Van Ettekoven K, Van der Arend A J M, 1999. identification and denomination of 'new' races of *Bremia lactucae*. In: Lebeda A, Kristkova E (eds.) Eucarpia leafy vegetables '99. Palacky University, Olomouc, Czech Republic, 1999: 171-175; Van der Arend, A. J. M., Gautier, J., Guenard, M., Michel, H., Moreau, B., de Ruijter, J., Schut, J. W. and de Witte, I. (2003). Identification and denomination of 'new' races of *Bremia lactucae* in Europe by IBEB until 2002. In: Eucarpia leafy vegetables 2003. Proceedings of the Eucarpia Meeting on leafy vegetables genetics and breeding. Noorwijkerhout, The Netherlands. Eds. Van Hintum T., Lebeda A., Pink D., Schut J. pp 151-160; Van der Arend A J M, Gautier J, Grimault V, Kraan P, Van der Laan R, Mazet J, Michel H, Schut J W, Smilde D, De Witte I (2006) Identification and denomination of "new" races of *Bremia lactucae* in Europe by IBEB until 2006; incorporated herein by reference; Plantum NL (Dutch association for breeding, tissue culture, production and trade of seeds and young plants), IBEB press release, " New race of *Bremia lactucae* Bl:27 identified and nominated", May 2010; Plantum NL (Dutch association for breeding, tissue culture, production and trade of seeds and young plants), IBEB press release, "New race of *Bremia lactucae* Bl:28 identified and nominated", March 2011; Plantum NL (Dutch association for breeding, tissue culture, production and trade of seeds and young plants), IBEB press release, "New races of *Bremia lactucae*, Bl:29, Bl:30 and Bl:31 identified and nominated", August 2013). Ca-I to Ca-VIII means Ca-I, Ca-IIA, Ca-IIB, Ca-III, Ca-IV (Schettini, T. M., Legg, E. J., Michelmore, R. W., 1991. Insensitivity to metalaxyl in California populations of *Bremia lactucae* and resistance of California lettuce cultivars to downy mildew, Phytopathology 81(1). p.64-'70), and Ca-V, Ca-VI, Ca-VII, Ca-VIII (Michelmore R. & Ochoa. O. "Breeding Crisphead Lettuce." In: California Lettuce Research Board, Annual Report 2005-2006, 2006, Salinas, Calif., pp. 55-68).

Resistance typically is tested by two interchangeable methods, described by Bonnier, F. J. M. et al. (Euphytica, 61(3):203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

As used herein, head size and plant size are defined on a scale from 1 to 9, according to the official guidelines of the European Union Community Plant Variety Office (Protocol for Distinctness Uniformity and Stability Tests; *Lactuca sativa* L.; Lettuce; CPVO-TP/13/5 Final; incorporated herein by reference). The person skilled in the art is familiar with the testing protocol and terminology used therein.

As used herein, head size is defined on a scale from 1 to 9. "1" being very small, comparable to variety Tom Thumb; "3" being small, comparable to varieties Bastion and Gotte a graine blanche; "5" Being medium, comparable to varieties Fiorella and Soraya; "7" being large, comparable to varieties great Lakes 659 and Musette; "9" being very large, comparable to varieties El Toro and Blonde maraichere. The head size of plants of lettuce variety 45-90 RZ is scored as very large. The heads have a size similar or even larger than that of standard variety El Toro.

As used herein, plant diameter is defined on a scale from 1 to 9. "1" being very small, comparable to varieties Pavane and Tom Thumb; "3" being small, comparable to varieties Bastion and Gotte a graine blanche; "5" Being medium, comparable to varieties Clarion and Verpia, "7" being large, comparable to varieties great Lakes 659 and Musette; "9" being very large, comparable to varieties El Toro and Yuma. The diameter of plants of lettuce variety 45-90 RZ is scored as very large. The diameter is similar or even larger than that of standard variety El Toro.

Leaf blistering in lettuce is the amount of bubbling or wrinkling of the leaves. Amongst lettuce varieties, different categories of blistering can be recognized. As used herein, blistering of the mature leaves is determined by comparison to standard varieties Salinas, Vanguard, and Prize Head, which have absent to slight, moderate, and strong blistering of the leaves, respectively. The blistering of leaves of 45-90 RZ is thus comparable to that of Vanguard.

Embodiments of the inventions advantageously have one or more, and most advantageously all, of these characteristics.

In Table 2, the seed color, cotyledon shape and characteristics of the fourth leaf of "45-90 RZ" are compared with "Umbrinas RZ", "45-03 RZ" and "Saladin".

TABLE 2

| Character | 45-90 RZ | Umbrinas RZ | 45-03 RZ | Saladin |
|---|---|---|---|---|
| Plant Type | Vanguard | Salinas | Salinas group | Salinas |
| Seed Color | Black | Black | Black | Black |
| Cotyledon Shape | Intermediate | Intermediate | Spatulate to intermediate | Intermediate |
| Shape of Fourth Leaf | Elongated | Elongated | Elongated | Elongated |
| Rolling of Fourth Leaf | Present | Present | Present | Present |
| Cupping of Fourth Leaf | Uncupped | Uncupped | Uncupped | Uncupped |
| Fourth Leaf Apical Margin | Entire | Entire | Entire | Entire |
| Fourth Leaf Basal Margin | Finely dentate | Finely dentate | Coarsely dentate | Finely dentate |
| Undulation | Slight to flat | Slight to flat | Flat to slight | Slight to flat |
| Green color | Grey green | Grey green | Dark green (greyish) | Grey green |
| Anthocyanin distribution | Absent | Absent | Absent | Absent |

In Table 3, the mature leaf and head characteristics of "45-90 RZ" are compared with "Umbrinas RZ", "45-03 RZ" and "Saladin". RHS=Royal Horticulural Society colour chart code.

TABLE 3

| Character | 45-90 RZ | Umbrinas RZ | 45-03 RZ | Saladin |
|---|---|---|---|---|
| Leaf Color | Grey green | Grey green | Medium green (greyish) | Grey green |
| Anthocyanin Distribution | Absent | Absent | Absent | Absent |
| Margin Incision Depth | Absent/shallow | Absent/shallow | Shallow | Absent/shallow |
| Margin Indentation | Shallowly dentate | Shallowly dentate | Shallowly dentate | Shallowly dentate |
| Undulations of the Apical Margin | Absent/slight | Absent/slight | Moderate to slight | Absent/slight |
| Leaf Size | Large | Medium to large | Medium to large | Large to medium |
| Leaf Glossiness | Dull | Dull | Dull to moderate | Dull |
| Leaf Blistering | Moderate | Slight to moderate | Strong | Moderate |
| Leaf Thickness | Thick | Thick | Intermediate to thick | Thick |
| Trichomes | Absent | Absent | Absent | Absent |
| Head Shape | Spherical to elongate | Spherical | Spherical | Spherical |
| Butt Shape | Rounded | Rounded | Rounded | Rounded |
| Midrib | Prominently raised | Prominently raised | Flattened | Moderately raised |

In an embodiment, the invention relates to lettuce plants that have all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that may be introduced by backcrossing, useful traits may be introduced directly into the plant of the invention, being a plant of lettuce variety 45-90 RZ, by genetic transformation techniques; and, such plants of lettuce variety 45-90 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of lettuce variety 45-90 RZ or may, alternatively, be used for the preparation of transgenes which may be introduced by backcrossing. Methods for the transformation of plants, including lettuce, are well known to those of skill in the art.

Vectors used for the transformation of lettuce cells are not limited so long as the vector may express an inserted DNA in the cells. For example, vectors which may comprise promoters for constitutive gene expression in lettuce cells (e.g., cauliflower mosaic virus 35S promoter) and promoters inducible by exogenous stimuli may be used. Examples of suitable vectors include pBI binary vector. The "lettuce cell" into which the vector is to be introduced includes various forms of lettuce cells, such as cultured cell suspensions, protoplasts, leaf sections, and callus. A vector may be introduced into lettuce cells by known methods, such as the polyethylene glycol method, polycation method, electroporation, Agrobacterium-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those which may be comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of lettuce variety 45-90 RZ.

Agrobacterium-mediated transfer is another widely applicable system for introducing gene loci into plant cells. An advantage of the technique is that DNA may be introduced into whole plant tissues, thereby bypassing the need for regeneration of an intact plant from a protoplast. Agrobacterium transformation vectors are capable of replication in *E. coli* as well as Agrobacterium, allowing for convenient manipulations. Moreover, advances in vectors for Agrobacterium-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, Agrobacterium containing both armed and disarmed Ti genes may be used for transformation. In those plant strains where Agrobacterium-mediated transformation is efficient, it is the method of choice because of the facile and defined nature of the gene locus transfer. The use of Agrobacterium-mediated plant integrating vectors to introduce DNA into plant cells, including lettuce plant cells, is well known in the art (See, e.g., U.S. Pats. Nos. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from lettuce (psaD, psaF, psaE, PC, FNR, atpC, atpD, cab, rbcS) (see U.S. Pat. No. 7,161,061), the CAB-1 promoter from lettuce (see U.S. Pat No. 7,663,027), the promoter from maize prolamin seed storage protein (see U.S. Pat No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wunl, or (5)

chemicals such as methyl jasmonate, salicylic acid, or Safener. It may also be advantageous to employ organ-specific promoters.

Exemplary nucleic acids which may be introduced to the lettuce variety of this invention include, for example, DNA sequences or genes from another species, or even genes or sequences which originate with or are present in lettuce species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of lettuce variety 45-90 RZ. Non-limiting examples of particular genes and corresponding phenotypes one may choose to introduce into a lettuce plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat No. 7,576,262, "Modified gene-silencing RNA and uses thereof")

U.S. Pats. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. Patents that may concern transformed lettuce and/or methods of transforming lettuce or lettuce plant cells, and techniques from these US Patents, as well as promoters, vectors, etc., may be employed in the practice of this invention to introduce exogenous nucleic acid sequence(s) into a plant of lettuce variety 45-90 RZ (or cells thereof), and exemplify some exogenous nucleic acid sequence(s) which may be introduced into a plant of lettuce variety 45-90 RZ (or cells thereof) of the invention, as well as techniques, promoters, vectors etc., to thereby obtain further plants of lettuce variety 45-90 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems. (See generally U.S. Pat No. 7,041,876 on lettuce being recognized as a plant that may be regenerated from cultured cells or tissue).

Also, the invention comprehends methods for producing a seed of a "45-90 RZ"-derived lettuce plant which may comprise (a) crossing a plant of lettuce variety 45-90 RZ, representative seed of which having been deposited under NCIMB Accession No. 42275, with a second lettuce plant, and (b) whereby seed of a 45-90 RZ-derived lettuce plant form. Such a method may further comprise (c) crossing a plant grown from 45-90 RZ-derived lettuce seed with itself or with a second lettuce plant to yield additional 45-90 RZ-derived lettuce seed, (d) growing the additional 45-90 RZ-derived lettuce seed of step (c) to yield additional 45-90 RZ-derived lettuce plants, and (e) repeating the crossing and growing of steps (c) and (d) for an additional 3-10 generations to further generate 45-90 RZ-derived lettuce plants.

The invention further relates to the above methods that may further comprise selecting at steps b), d), and e), a 45-90 RZ-derived lettuce plant, exhibiting a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

In particular, the invention relates to methods for producing a seed of a 45-90 RZ-derived lettuce plant which may comprise (a) crossing a plant of lettuce variety 45-90 RZ, representative seed of which having been deposited under NCIMB Accession No. 42275, with a second lettuce plant and (b) whereby seed of a 45-90 RZ-derived lettuce plant forms, wherein such a method may further comprise (c) crossing a plant grown from 45-90 RZ-derived lettuce seed with itself or with a second lettuce plant to yield additional 45-90 RZ-derived lettuce seed, (d) growing the additional 45-90 RZ-derived lettuce seed of step (c) to yield additional 45-90 RZ-derived lettuce plants and selecting plants exhibiting a combination of the traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, and (e) repeating the crossing and growing of steps (c) and (d) for an additional 3-10 generations to further generate 45-90 RZ-derived lettuce plants that exhibit a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

The invention additionally provides a method of introducing a desired trait into a plant of lettuce variety 45-90 RZ which may comprise: (a) crossing a plant of lettuce variety 45-90 RZ, representative seed of which having been deposited under NCIMB Accession No. 42275, with a second lettuce plant that may comprise a desired trait to produce F1 progeny; (b) selecting an F1 progeny that may comprise the desired trait; (c) crossing the selected F1 progeny with a plant of lettuce variety 45-90 RZ, to produce backcross progeny; (d) selecting backcross progeny which may comprise the desired trait and the physiological and morphological characteristic of a plant of lettuce variety 45-90 RZ; and, optionally, (e) repeating steps (c) and (d) one or more times in succession to produce selected fourth or higher backcross progeny that may comprise the desired trait and all of the physiological and morphological characteristics of a plant of lettuce variety 45-90 RZ, when grown in the same environmental conditions. The invention, of course, includes a lettuce plant produced by this method.

Backcrossing may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When a plant of lettuce variety 45-90 RZ, representative seed of which having been deposited under NCIMB Accession No. 42275, is used in backcrossing, offspring retaining the combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves are progeny within the ambit of the invention. Backcrossing methods may be used with the present invention to improve or introduce a characteristic into a plant of the invention, being a plant of lettuce variety 45-90 RZ. See, e.g., U.S. Pat. No. 7,705,206 (incorporated herein by reference consistent with the above INCORPORATION BY REFERENCE section), for a general discussion relating to backcrossing.

The invention further involves a method of determining the genotype of a plant of lettuce variety 45-90 RZ, representative seed of which has been deposited under NCIMB Accession No. 42275, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of lettuce variety 45-90 RZ.

There are various ways of obtaining genotype data from a nucleic acid sample. Genotype data may be gathered which is specific for certain phenotypic traits (e.g. gene sequences), but also patterns of random genetic variation may be obtained to construct a so-called DNA fingerprint. Depending on the technique used a fingerprint may be obtained that is unique for lettuce variety 45-90 RZ. Obtaining a unique DNA fingerprint depends on the genetic variation present in a variety and the sensitivity of the fingerprinting technique. A technique known in the art to provide a good fingerprint profile is called AFLP fingerprinting technique (See generally U.S. Pat No. 5,874,215), but there are many other marker based techniques, such as RFLP (or Restriction fragment length polymorphism), SSLP (or Simple sequence length polymorphism), RAPD (or Random amplification of polymorphic DNA) VNTR (or Variable number tandem repeat), Microsatellite polymorphism, SSR (or Simple sequence repeat), STR (or Short tandem repeat), SFP (or Single feature polymorphism) DArT (or Diversity Arrays Technology), RAD markers (or Restriction site associated DNA markers) (e.g. Baird et al. PloS One Vol. 3 e3376, 2008; Semagn et al. African Journal of Biotechnology Vol. 5 number 25 pp. 2540-2568, 29 Dec. 2006). Nowadays, sequence-based methods are utilizing Single Nucleotide Polymorphisms (SNPs) that are randomly distributed across genomes, as a common tool for genotyping (e.g. Elshire et al. PloS One Vol. 6: e19379, 2011; Poland et al. PloS One Vol. 7: e32253; Truong et al. PLoS One Vol. 7 number 5: e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species. For example, it is possible to detect polymorphisms for the characteristic of *Bremia* resistance by comparing the genotype and/or the sequence of lettuce variety 45-90 RZ with the genotype and/or the sequence of one or more reference plants. The reference plant(s) used for comparison in this example may for example be, but is not limited to, any of the comparison varieties 45-03 RZ, Umbrinas or Saladin. It is also possible for example, to detect polymorphisms for head size by comparing the genotype and/or the sequence of lettuce variety 45-90 RZ with the genotype and/or the sequence of one or more reference plants. The reference plant(s) used for comparison may for example be, but is not limited to, any of the comparison varieties 45-03 RZ, Umbrinas or Saladin.

The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

Lettuce leaves are sold in packaged form, including without limitation as pre-packaged lettuce salad or as lettuce heads. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the lettuce leaves of the invention. Thus, the invention comprehends the use of and methods for making and using the leaves of the lettuce plant of the invention, as well as leaves of lettuce plants derived from the invention. The invention further relates to a container which may comprise one or more plants of the invention, or one or more lettuce plants derived from a plant of the invention, in a growth substrate for harvest of leaves from the plant in a domestic environment. This way the consumer may pick very fresh leaves for use in salads. More generally, the invention includes one or more plants of the invention or one or more plants derived from lettuce of the invention, wherein the plant is in a ready-to-harvest condition, including with the consumer picking his own, and further including a container which may comprise one or more of these plants.

The invention is further described by the following numbered paragraphs:
1. A lettuce plant designated 45-90 RZ, representative seed of which having been deposited under NCIMB Accession No. 42275, wherein said plant comprises at least the following combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.
2. The lettuce plant of paragraph 1 wherein the plant is resistant against root aphid.
3. A seed of the plant of paragraph 1.
4. Parts of the plant of paragraph 1, wherein said parts of the plant are suitable for sexual reproduction.
5. Parts of the plant of paragraph 4, wherein said parts are selected from the group consisting of microspores, pollen, ovaries, ovules, embryo sacs and egg cells.
6. Parts of the plant of paragraph 1, wherein said parts of the plant are suitable for vegetative reproduction.
7. Parts of paragraph 6, wherein said parts are selected from the group consisting of cuttings, roots, stems, cells and protoplasts.
8. A tissue culture of regenerable cells from the lettuce plant of paragraph 1.
9. The tissue culture of paragraph 8, wherein said cells or protoplasts of the tissue culture which are derived from a tissue selected from the group consisting of leaves, pollen, embryos, cotyledon, hypocotyls, meristematic cells, roots, root tips, anthers, flowers, seeds and stems.
10. A method for producing a progeny plant of a lettuce plant of paragraph 1, comprising crossing the plant of paragraph 1 with itself or with another lettuce plant, harvesting the resultant seed, and growing said seed.
11. A progeny plant produced by the method of paragraph 10, wherein said progeny exhibits a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.
12. A progeny plant produced by the method of paragraph 10, wherein said progeny plant has all the morphological and physiological characteristics of the lettuce plant designated 45-90 RZ, representative seed of which having been deposited under NCIMB Accession No. 42275, wherein said plant comprises at least the following combination of traits resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.
13. A progeny plant produced by the method of paragraph 10, wherein said progeny plant, representative seed of which having been deposited under NCIMB Accession 42275, is modified in one or more other characteristics.
14. The progeny of paragraph 13, wherein the modification is effected by mutagenesis.
15. The of paragraph 13, wherein the modification is effected by transformation with a transgene.
16. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of paragraph 1.
17. A hybrid lettuce plant produced by the method of paragraph 16.
18. A method of producing a lettuce cultivar containing a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, comprising: crossing a mother lettuce plant with a father lettuce plant to produce a hybrid seed; growing said hybrid seed to produce a hybrid plant; selfing said hybrid plant to produce F2 progeny seed; growing said F2 progeny seed to produce F2-plants; selecting said F2-plants for exhibiting resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, and, selfing said selected F2-plants to produce F3 progeny seed; growing said F3 progeny seed to produce F3-plants; selecting F3-plants for exhibiting resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, optionally followed by more selfing and selection steps.

19. A lettuce cultivar produced by the method of paragraph 18.

20. A method for producing lettuce leaves as a fresh vegetable comprising packaging leaves of a plant of paragraph 1.

21. A method for producing lettuce leaves as a processed food comprising processing leaves of a plant of paragraph 1.

22. One or more lettuce plants of paragraph 1, in a container, for harvest of leaves.

23. A lettuce plant having morphological and/or physiological characteristics of a lettuce plant, representative seed of which having been deposited under NCIMB Accession No. 42275.

24. A method of introducing a desired trait into a plant of lettuce variety 45-90 RZ comprising: (a) crossing a plant of lettuce variety 45-90 RZ, representative seed of which having been deposited under NCIMB Accession No. 42275, with a second lettuce plant that comprises the desired trait to produce F1 progeny; (b) selecting an F1 progeny that comprises the desired trait; (c) crossing the selected F1 progeny with a plant of lettuce variety 45-90 RZ, to produce backcross progeny and (d) selecting backcross progeny comprising the desired trait and the physiological and morphological characteristic of a plant of lettuce variety 45-90 RZ, when grown in the same environmental conditions.

25. The method of paragraph 24 further comprising (e) repeating steps (c) and (d) one or more times in succession to produce selected fourth or higher backcross progeny that comprise the desired trait and all of the physiological and morphological characteristics of a plant of lettuce variety 45-90 RZ, when grown in the same environmental conditions.

26. A lettuce plant produced by the method of paragraph 24 or 25.

27. A method for producing a seed of a 45-90 RZ-derived lettuce plant comprising (a) crossing a plant of lettuce variety 45-90 RZ, representative seed of which having been deposited under NCIMB Accession No. 42275, with a second lettuce plant, and (b) whereby seed of a 45-90 RZ-derived lettuce plant form.

28. The method of paragraph 27 further comprising (c) crossing a plant grown from 45-90 RZ-derived lettuce seed with itself or with a second lettuce plant to yield additional 45-90 RZ-derived lettuce seed, (d) growing the additional 45-90 RZ-derived lettuce seed of step (c) to yield additional 45-90 RZ-derived lettuce plants, and (e) repeating the crossing and growing of steps (c) and (d) for an additional 3-10 generations to generate further 45-90 RZ-derived lettuce plants.

29. The method of paragraph 27 or 28 further comprising selecting at steps b), d), and e), a 45-90 RZ-derived lettuce plant, exhibiting a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

30. A seed produced by the method of paragraphs 27, 28, or 29.

31. A method of determining the genotype of a plant of lettuce variety 45-90 RZ, representative seed of which has been deposited under NCIMB Accession No. 42275, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of lettuce variety 45-90 RZ and/or give rise to the expression of any one or more, or all, of the morphological and physiological characteristics of lettuce variety 45-90 RZ of paragraph 1.

32. The method of paragraph 31 additionally comprising the step of storing the results of detecting the plurality of polymorphisms on a computer readable medium, or transmitting the results of detecting the plurality of polymorphisms.

33. The computer readable medium of paragraph 32.

34. A lettuce plant exhibiting a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, and having genetic information for so exhibiting the combination of traits, wherein the genetic information is as contained in a plant, representative seed of which having been deposited under NCIMB Accession No. NCIMB 42275.

35. The lettuce plant of paragraph 1, which is grown from seed having been deposited under NCIMB Accession No. 42275.

36. A lettuce plant having all the morphological and physiological characteristics of the lettuce plant of paragraph1, representative seed of which having been deposited under NCIMB Accession No. NCIMB 42275.

37. A hybrid lettuce plant grown from the seed of paragraph 17.

\* \* \*

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A lettuce plant designated 45-90 RZ, representative seed of which having been deposited under NCIMB Accession No. 42275, wherein said plant comprises at least the following combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

2. A seed of the plant of claim 1.

3. A part of the plant of claim 1, wherein said part of the plant is suitable for sexual reproduction.

4. The part of the plant as claimed in claim 3, wherein said part comprises a microspore, pollen, ovary, ovule, embryo sac or egg cell.

5. A part of the plant of claim 1, wherein said part of the plant is suitable for vegetative reproduction.

6. The part of the plant as claimed in claim 5, wherein said part comprises a cutting, root, stem, cell or protoplast.

7. A tissue culture of regenerable cells or protoplasts from the lettuce plant of claim 1.

8. The tissue culture as claimed in claim 7, wherein said cells or protoplasts of the tissue culture are derived from a tissue comprising a leaf, pollen, embryo, cotyledon, hypocotyl, meristematic cell, root, root tip, anther, flower, seed or stem.

9. A method for producing a progeny plant of a lettuce plant of claim 1, comprising crossing the plant of claim 1 with itself or with another lettuce plant, harvesting the resultant seed, and growing said seed.

10. A progeny plant produced by the method of claim 9, wherein said progeny exhibits a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

11. The progeny plant of claim 10, wherein said progeny plant is further modified in one or more other characteristics.

12. The progeny as claimed in claim 11, wherein the modification is effected by mutagenesis.

13. The progeny as claimed in claim 11, wherein the modification is effected by transformation with a transgene.

14. A progeny plant produced by the method of claim 9, wherein said progeny plant has all the morphological and physiological characteristics of the lettuce plant designated 45-90 RZ.

15. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1.

16. A hybrid lettuce seed produced by the method of claim 15.

17. A hybrid lettuce plant grown from the seed of claim 16.

18. A method for producing lettuce leaves as a fresh vegetable comprising packaging leaves of a plant of claim 1.

19. A method for producing lettuce leaves as a processed food comprising processing leaves of a plant of claim 1.

20. A container comprising one or more lettuce plants of claim 1 for harvest of leaves.

21. A method of determining the genotype of a plant of lettuce variety 45-90 RZ, representative seed of which has been deposited under NCIMB Accession No. 42275, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of lettuce variety 45-90 RZ and/or give rise to the expression of any one or more, or all, of the morphological and physiological characteristics of lettuce variety 45-90 RZ as claimed in claim 1.

22. The method of claim 21 additionally comprising the step of storing the results of detecting the plurality of polymorphisms on a computer readable medium, or transmitting the results of detecting the plurality of polymorphisms.

23. A lettuce plant having all the morphological and physiological characteristics of the lettuce plant of claim 1, representative seed of which having been deposited under NCIMB Accession No. 42275.

24. The lettuce plant of claim 1, which is grown from seed having been deposited under NCIMB Accession No. 42275.

25. A method of producing a lettuce cultivar containing a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, representative seed of which having been deposited under NCIMB Accession No. 42275, comprising: crossing a mother lettuce plant with a father lettuce plant to produce a hybrid seed; growing said hybrid seed to produce a hybrid plant; selfing said hybrid plant to produce F2, progeny seed; growing said F2, progeny seed to produce F2-plants; selecting said F2-plants for exhibiting resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, and, selfing said selected F2-plants to produce F3, progeny seed; growing said F3, progeny seed to produce F3-plants; selecting F3-plants for exhibiting resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, representative seed of which having been deposited under NCIMB Accession No. 42275, optionally followed by more selfing and selection steps.

26. A lettuce cultivar produced by the method of claim 25.

27. A lettuce plant having resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves and other morphological and/or physiological characteristics of a lettuce plant, representative seed of which having been deposited under NCIMB Accession No. 42275.

28. A method of introducing a desired trait into a plant of lettuce variety 45-90 RZ comprising: (a) crossing a plant of lettuce variety 45-90 RZ, representative seed of which having been deposited under NCIMB Accession No. 42275, with a second lettuce plant that comprises the desired trait to produce F1 progeny; (b) selecting an F1progeny that comprises the desired trait; (c) crossing the selected F1 progeny with a plant of lettuce variety 45-90 RZ, to produce backcross progeny and (d) selecting backcross progeny comprising the desired trait and physiological and morphological characteristics of a plant of lettuce variety 45-90 RZ, when grown in the same environmental conditions.

29. The method of claim 28 further comprising (e) repeating steps (c) and (d) one or more times in succession to produce selected fourth or higher backcross progeny that comprise the desired trait and all of the physiological and morphological characteristics of a plant of lettuce variety 45-90 RZ, when grown in the same environmental conditions.

30. A lettuce plant produced by the method of claim 28.

31. A method for producing a seed of a 45-90 RZ-derived lettuce plant comprising (a) crossing a plant of lettuce variety 45-90 RZ, representative seed of which having been deposited under NCIMB Accession No. 42275, with a second lettuce plant, and (b) whereby seed of a 45-90 RZ-derived lettuce plant forms.

32. The method of claim 31 further comprising (c) crossing a plant grown from 45-90 RZ-derived lettuce seed with itself or with a second lettuce plant to yield additional 45-90 RZ-derived lettuce seed, (d) growing the additional 45-90 RZ-derived lettuce seed of step (c) to yield additional 45-90 RZ-derived lettuce plants, and (e) repeating the crossing and growing of steps (c) and (d) for an additional 3-10 generations to generate further 45-90 RZ-derived lettuce plants.

33. The method of claim 32 further comprising selecting at steps b), d), and e), a 45-90 RZ-derived lettuce plant, exhibiting a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves.

34. A seed produced by the method of claim 31.

35. A lettuce plant exhibiting a combination of traits including resistance against downy mildew (*Bremia lactucae*) races Bl:1-26, Bl:28, Bl:31, CA-I, CA-IIA, CAIIB, CA-III, CA-IV, CA-VI, CA-VII, and CA-VIII, and has a very large head size, very large plant diameter, and large sized leaves, and having genetic information for so exhibiting the combination of traits, wherein the genetic information is as contained in a plant, representative seed of which having been deposited under NCIMB Accession No. 42275.

* * * * *